United States Patent
Hoffmann et al.

(10) Patent No.: US 7,597,689 B2
(45) Date of Patent: Oct. 6, 2009

(54) DISPOSABLE ABSORBENT ARTICLE WITH IMPROVED TOPSHEET

(75) Inventors: Anja Hoffmann, Hofheim (DE); Joerg Mueller, Karben (DE); Heike Opper, Bad Soden (DE); Georg Pescher, Trelissac Cedex (FR); Mattias Schmidt, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 458 days.

(21) Appl. No.: 10/703,233

(22) Filed: Nov. 7, 2003

(65) Prior Publication Data

US 2004/0092900 A1   May 13, 2004

(30) Foreign Application Priority Data

Nov. 8, 2002   (EP) ................... 02024879

(51) Int. Cl.
*A61F 13/15* (2006.01)
*A61F 13/20* (2006.01)

(52) U.S. Cl. .............. 604/385.101; 604/378; 604/385.01

(58) Field of Classification Search ............ 604/384, 604/385.19, 385.09, 380
See application file for complete search history.

(56) References Cited

U.S. PATENT DOCUMENTS

| | | | |
|---|---|---|---|
| 2,043,325 A | 6/1936 | Jackson | |
| 2,277,043 A | 3/1942 | Cohn | |
| 2,532,029 A | 11/1950 | Medoff | |
| 2,690,749 A | 10/1954 | Nelson | |
| 2,837,095 A | 6/1958 | Stevenson | |
| 3,214,323 A * | 10/1965 | Gordon et al. | 428/198 |
| 3,367,333 A * | 2/1968 | Scheier | 604/375 |
| 3,447,536 A | 6/1969 | Snyder | |
| 3,468,748 A | 9/1969 | Bassett | |
| 3,626,943 A | 12/1971 | Worcester | |
| 3,848,594 A | 11/1974 | Buell | |

(Continued)

FOREIGN PATENT DOCUMENTS

EP   0 286 543 A2   10/1988

(Continued)

OTHER PUBLICATIONS

U.S. Appl. No. 11/786,890, filed Apr. 13, 2007, Mueller, et al.

(Continued)

*Primary Examiner*—Michele Kidwell
(74) *Attorney, Agent, or Firm*—Charles R. Matson; George H. Leal; Jay A. Krebs (57) ABSTRACT

A disposable absorbent article with a backsheet and a first topsheet, is capable of being at least partially in contact with the wearer's skin when in use. The first topsheet being a fibrous three-dimensional web, having bonded regions where the fibers are bonded to another, and unbonded regions, where the fibers are unbonded to one another. The fibers extend from at least one unbonded region into at least two bonded regions, typically in the form of loops. The bonded regions form the support structure for the unbonded regions, and the surface area of the unbonded regions is at least 2 mm$^2$. The topsheet has a thickness (caliper) of between 0.1 and 5 mm.

15 Claims, 4 Drawing Sheets

U.S. PATENT DOCUMENTS

| | | | |
|---|---|---|---|
| 3,855,046 A | 12/1974 | Hansen et al. | |
| 3,860,003 A | 1/1975 | Buell | |
| 3,890,973 A | 6/1975 | Davis et al. | |
| RE28,483 E | 7/1975 | Ralph | |
| 3,918,433 A | 11/1975 | Fuisz | |
| 3,929,135 A | 12/1975 | Thompson | |
| 4,324,246 A | 4/1982 | Mullane et al. | |
| 4,333,979 A | 6/1982 | Sciaraffa et al. | |
| 4,342,314 A | 8/1982 | Radel et al. | |
| 4,463,045 A | 7/1984 | Ahr et al. | |
| 4,515,595 A | 5/1985 | Kievit et al. | |
| 4,559,051 A | 12/1985 | Hanson | |
| 4,573,986 A | 3/1986 | Minetola et al. | |
| 4,609,518 A | 9/1986 | Curro et al. | |
| 4,610,678 A | 9/1986 | Weisman et al. | |
| 4,610,685 A | 9/1986 | Raley | |
| 4,629,643 A | 12/1986 | Curro et al. | |
| 4,662,875 A | 5/1987 | Hirotsu et al. | |
| 4,662,877 A * | 5/1987 | Williams | 604/385.27 |
| 4,673,402 A | 6/1987 | Weisman et al. | |
| 4,678,464 A | 7/1987 | Holtman | |
| 4,681,577 A | 7/1987 | Stern et al. | |
| 4,695,278 A | 9/1987 | Lawson | |
| 4,704,116 A | 11/1987 | Enloe | |
| RE32,649 E | 4/1988 | Brandt et al. | |
| 4,778,459 A | 10/1988 | Fuisz | |
| 4,795,454 A | 1/1989 | Dragoo | |
| 4,808,178 A | 2/1989 | Aziz et al. | |
| 4,834,735 A | 5/1989 | Alemany et al. | |
| 4,834,737 A | 5/1989 | Khan | |
| 4,846,815 A | 7/1989 | Scripps | |
| 4,888,231 A | 12/1989 | Angstadt | |
| 4,892,536 A | 1/1990 | DesMarais et al. | |
| 4,894,060 A | 1/1990 | Nestegard | |
| 4,909,803 A | 3/1990 | Aziz et al. | |
| 4,946,527 A | 8/1990 | Battrell | |
| 4,963,140 A | 10/1990 | Robertson et al. | |
| 4,988,344 A | 1/1991 | Reising | |
| 4,988,345 A | 1/1991 | Reising | |
| 4,990,147 A | 2/1991 | Freeland | |
| 5,062,840 A | 11/1991 | Holt et al. | |
| 5,069,677 A * | 12/1991 | Sakurai et al. | 604/370 |
| 5,137,537 A | 8/1992 | Herron et al. | |
| 5,147,345 A | 9/1992 | Young et al. | |
| 5,151,092 A | 9/1992 | Buell et al. | |
| 5,156,911 A | 10/1992 | Stewart | |
| 5,176,672 A | 1/1993 | Bruemmer et al. | |
| 5,192,606 A | 3/1993 | Proxmire et al. | |
| 5,209,801 A | 5/1993 | Smith | |
| 5,221,274 A | 6/1993 | Buell et al. | |
| 5,260,345 A | 11/1993 | DesMarais et al. | |
| 5,306,266 A | 4/1994 | Freeland | |
| 5,316,836 A | 5/1994 | Heindel et al. | |
| 5,322,729 A | 6/1994 | Heeter et al. | |
| 5,330,459 A | 7/1994 | Lavon et al. | |
| 5,332,897 A | 7/1994 | Stobbe et al. | |
| 5,336,545 A | 8/1994 | Morman | |
| 5,342,338 A | 8/1994 | Roe | |
| 5,344,516 A | 9/1994 | Tanji et al. | |
| 5,382,400 A | 1/1995 | Pike et al. | |
| 5,382,703 A | 1/1995 | Nohr et al. | |
| 5,387,207 A | 2/1995 | Dyer et al. | |
| 5,387,450 A | 2/1995 | Stewart | |
| 5,397,316 A | 3/1995 | Lavon et al. | |
| 5,429,632 A | 7/1995 | Tanji et al. | |
| 5,439,459 A | 8/1995 | Tanji et al. | |
| 5,439,734 A | 8/1995 | Everhart et al. | |
| 5,462,541 A | 10/1995 | Bruemmer et al. | |
| 5,494,736 A | 2/1996 | Willey et al. | |
| 5,514,121 A | 5/1996 | Roe et al. | |
| 5,518,801 A | 5/1996 | Chappell et al. | |
| 5,520,673 A | 5/1996 | Yarbrough et al. | |
| 5,520,674 A | 5/1996 | Lavon et al. | |
| 5,536,555 A * | 7/1996 | Zelazoski et al. | 428/138 |
| 5,567,478 A | 10/1996 | Houben et al. | |
| 5,576,091 A | 11/1996 | Zajaczkowski et al. | |
| 5,576,282 A | 11/1996 | Miracle et al. | |
| 5,607,760 A | 3/1997 | Roe | |
| 5,609,587 A | 3/1997 | Roe | |
| 5,611,791 A * | 3/1997 | Gorman et al. | 604/391 |
| 5,623,888 A | 4/1997 | Zafiroglu | |
| 5,625,222 A | 4/1997 | Yoneda et al. | |
| 5,628,097 A | 5/1997 | Benson et al. | |
| 5,635,191 A | 6/1997 | Roe et al. | |
| H1670 H | 7/1997 | Aziz et al. | |
| 5,643,588 A | 7/1997 | Roe et al. | |
| 5,648,167 A | 7/1997 | Peck | |
| 5,658,639 A | 8/1997 | Curro et al. | |
| 5,667,619 A | 9/1997 | Alikhan | |
| 5,707,950 A | 1/1998 | Kasturi et al. | |
| 5,728,081 A | 3/1998 | Baer et al. | |
| 5,830,203 A | 11/1998 | Suzuki et al. | |
| 5,830,604 A | 11/1998 | Singleton et al. | |
| 5,853,403 A | 12/1998 | Tanzer et al. | |
| 5,858,515 A | 1/1999 | Stokes et al. | |
| 5,876,753 A | 3/1999 | Timmons et al. | |
| 5,888,591 A | 3/1999 | Gleason et al. | |
| 5,902,297 A | 5/1999 | Sauer | |
| 5,919,177 A | 7/1999 | Georger et al. | |
| 5,922,417 A | 7/1999 | Singleton et al. | |
| 5,941,864 A | 8/1999 | Roe | |
| 5,989,478 A | 11/1999 | Ouellette et al. | |
| 5,990,377 A * | 11/1999 | Chen et al. | 604/381 |
| 6,015,936 A | 1/2000 | Takai et al. | |
| 6,045,877 A | 4/2000 | Gleason et al. | |
| 6,168,583 B1 | 1/2001 | Tanji et al. | |
| 6,186,992 B1 * | 2/2001 | Roe et al. | 604/385.01 |
| 6,261,679 B1 | 7/2001 | Chen et al. | |
| 6,353,149 B1 | 3/2002 | Stone | |
| 6,380,456 B1 | 4/2002 | Goldman | |
| 6,395,957 B1 * | 5/2002 | Chen et al. | 604/381 |
| 6,417,425 B1 | 7/2002 | Whitmore et al. | |
| 6,461,430 B1 | 10/2002 | Kwok | |
| 6,465,073 B1 | 10/2002 | Morman et al. | |
| 6,482,191 B1 | 11/2002 | Roe et al. | |
| 6,537,695 B2 | 3/2003 | McLoughlin et al. | |
| 6,569,275 B1 | 5/2003 | Popp et al. | |
| 6,863,959 B2 | 3/2005 | Welch et al. | |
| 7,144,957 B2 | 12/2006 | Funk et al. | |
| 7,223,261 B2 | 5/2007 | Mueller et al. | |
| 2001/0000795 A1 * | 5/2001 | Bolian et al. | 604/381 |
| 2002/0029024 A1 * | 3/2002 | Furuya et al. | 604/378 |
| 2002/0049419 A1 * | 4/2002 | Mizutani et al. | 604/384 |
| 2002/0087136 A1 | 7/2002 | Widlund | |
| 2002/0119722 A1 | 8/2002 | Welch et al. | |
| 2002/0177632 A1 | 11/2002 | Choi | |
| 2003/0143376 A1 * | 7/2003 | Toyoshima et al. | 428/156 |
| 2003/0171729 A1 * | 9/2003 | Kaun et al. | 604/382 |
| 2004/0092900 A1 | 5/2004 | Hoffman et al. | |
| 2004/0092902 A1 | 5/2004 | Hoffman et al. | |
| 2004/0097895 A1 | 5/2004 | Busam et al. | |
| 2004/0162538 A1 | 8/2004 | Mueller et al. | |
| 2005/0004541 A1 | 1/2005 | Roberts | |
| 2005/0095942 A1 | 5/2005 | Mueller et al. | |
| 2005/0177123 A1 | 8/2005 | Catalan | |
| 2005/0215965 A1 | 9/2005 | Schmidt et al. | |
| 2006/0025744 A1 | 2/2006 | Mishima et al. | |
| 2007/0191806 A1 | 8/2007 | Mueller et al. | |
| 2007/0197992 A1 | 8/2007 | Martynus et al. | |

FOREIGN PATENT DOCUMENTS

| | | |
|---|---|---|
| EP | 0 357 298 A2 | 3/1990 |
| EP | 0 433 951 A2 | 6/1991 |

| | | |
|---|---|---|
| EP | 312118 B1 | 2/1996 |
| EP | 0 811 479 A2 | 12/1997 |
| EP | 0 934 736 A1 | 8/1999 |
| EP | 0 953 323 A | 11/1999 |
| EP | 978264 A1 * | 2/2000 |
| EP | 1 057 464 A2 | 12/2000 |
| EP | 1 106 152 A | 6/2001 |
| EP | 1 184 020 A2 | 3/2002 |
| EP | 1 190 690 A2 | 3/2002 |
| EP | 1 201 212 A | 5/2002 |
| EP | 1 279 388 A1 | 1/2003 |
| EP | 1 403 419 A | 3/2004 |
| GB | 2 284 550 A | 6/1995 |
| GB | 2 287 888 A | 10/1995 |
| GB | 2288412 A | 10/1995 |
| GB | 2 297 473 A | 8/1996 |
| GB | 2 328 158 A | 2/1999 |
| GB | 2 329 842 A | 4/1999 |
| JP | 07-136211 | 5/1995 |
| JP | 10-192342 | 7/1998 |
| WO | WO 93/01780 A1 | 2/1993 |
| WO | WO 93/16669 A1 | 9/1993 |
| WO | WO 95/09261 A1 | 4/1995 |
| WO | WO 95/24173 A2 | 9/1995 |
| WO | WO 96/00549 A1 | 1/1996 |
| WO | WO 96/03501 A1 | 2/1996 |
| WO | WO 96/13989 A1 | 5/1996 |
| WO | WO 98/08476 A1 | 3/1998 |
| WO | WO 98/43587 A1 | 10/1998 |
| WO | WO 98/56326 A1 | 12/1998 |
| WO | WO 99/02393 A1 | 1/1999 |
| WO | WO 99/02395 A1 | 1/1999 |
| WO | WO 99/27879 | 6/1999 |
| WO | WO 99/30661 A1 | 6/1999 |
| WO | WO 99/56680 A1 | 11/1999 |
| WO | WO 99/62446 A1 | 12/1999 |
| WO | WO 00/01334 A1 | 1/2000 |
| WO | WO 01/00053 A1 | 1/2001 |
| WO | WO 01/06974 A1 | 2/2001 |
| WO | WO 02/48440 A2 | 6/2002 |
| WO | WO 03/009795 | 2/2003 |
| WO | WO 2006/031639 A1 | 3/2006 |

OTHER PUBLICATIONS

U.S. Appl. No. 11/701,152, filed Feb. 1, 2007, Martynus, et al.

* cited by examiner

DISPOSABLE ABSORBENT ARTICLE WITH IMPROVED TOPSHEET

FIELD OF THE INVENTION

This invention is directed to disposable absorbent articles, such as diapers, training pants, adult incontinence articles, feminine protection articles and the like having a specific self-supporting fibrous topsheet with unbonded loop-shape fibers which immobilize runny bowel movement waste (hereinafter referred to as BM) effectively.

BACKGROUND OF THE INVENTION

In the last decade, there has been much research on topsheets that have an opening, which leads to a void space to receive or store BM. The focus has mainly been to reduce leakage from the diaper by improving the positioning of the opening against the wearer's body and in proximity of the anus of the wearer, for example by use of elastication means around the opening in the topsheet.

The inventors have found that the BM leakage problem is not only or not mainly caused by BM which is not received through the opening in the topsheet, but that an important part of the leakage problem is caused by BM which leaks back out of the storage space. The inventors have now found that the BM leakage problem of such diapers can be reduced when an additional topsheet (herein referred to as first topsheet) is provided underneath the topsheet with the opening, whereby the second topsheet traps the BM received through said opening.

In recent years, diaper manufacturers have done research on such diaper topsheets that can immobilize or trap BM, so that BM leakage from the diaper can be reduced. It has for example been suggested to incorporate in a diaper BM modifying agents, which for example change the viscosity of the BM material. Also suggested are, for example in WO99/56680 and EP-A-1057464, is the use of topsheets that comprise a backing material with thereon anchor portions with fibers that vertically extend from the backing layer and trap the BM. WO99/62446 and EP-A-1190690 describes loop-shaped fibers that are attached to such a backing sheet and which are said to trap BM material.

These suggested topsheet materials typically require a large volume (thickness) in order to store large quantities of BM and they are designed such that they can even store the BM under a certain pressure, e.g. when a baby is sitting. Subsequently, the suggested topsheets are typically thick and quite rough materials, which are thus not very comfortable. Furthermore, some of the topsheet materials suggested in the art are quite complex or difficult to produce, for example involving complex steps to anchor fibers to backing sheets. The use of these types of materials in diapers is thus not very economical.

There is thus still a need for diapers with an alternative BM trapping topsheet, which not only provides good BM trapping but which is also soft and comfortable in use.

The inventors have now found a diaper with such an alternative topsheet, which can be effectively used in diapers with a second topsheet with an opening, as described above. The topsheet has a supporting structure of regions where large fibers are bonded to one another and large regions (which do not contribute to the supporting structure) where the fibers are unbonded and extend in a loop-shape from the surface, and which trap the BM.

Because no backing sheet is needed as supporting structure, the tosphseet is soft, thin, comfortable, and more economical. Diapers with this type of topsheet are found to have much less BM leakage and less BM deposition on the wearer's skin, whilst still being very soft and comfortable.

SUMMARY OF THE INVENTION

The present invention relates to a disposable absorbent article with a backsheet and a first topsheet, which in use is capable of being at least partially in contact with the wearer's skin. The first topsheet is a three-dimensional web of fibres, having a width, length and thickness dimension. The web has bonded regions, where the fibres are bonded to another, and unbonded regions, where the fibres are unbonded to one another, whereby the fibres extend from at least one unbonded region into at least two bonded regions. The bonded regions form the support structure for the unbonded regions, and the surface area of the unbonded regions is at least 2 mm$^2$. The topsheet has a thickness of between 0.1 and 5 mm, as measured under a 0.09 psi (620 Pa) pressure, as described herein.

Typically, a part of the fibers in the unbonded regions are in the form of loops that extend in one direction out of the plane of said support structure, and another part of the fibers is in the form of loops that extend in the opposite direction, out of the plane of the support structure.

Typically, the first tospheet is a unitary sheet or web. Preferably, the first topsheet is a carded web, as described herein.

Preferably, the disposable, wearable absorbent article is a diaper or training pants, which preferably has a second topsheet, overlaying the first topsheet on the body facing side thereof, which has a large opening, to receive the BM through as described herein.

DETAILED DESCRIPTION OF THE INVENTION

As used herein, the following terms have the following meanings:

'Absorbent article' refers to wearable devices, which absorb and/or contain liquid, and more specifically, refers to devices, which are placed against or in proximity to the body of the wearer to absorb and contain the various exudates discharged from the body.

'Longitudinal' is a direction running parallel to the maximum linear dimension, typically the longitudinal axis, of the article and includes directions within 45° of the longitudinal direction. 'Length' of the article or component thereof, when used herein, generally refers to the size/distance of the maximum linear dimension, or typically to the size/distance of the longitudinal axis, of an article or part thereof.

The 'lateral' or 'transverse' direction is orthogonal to the longitudinal direction, i.e. in the same plan of the majority of the article and the longitudinal axis, and the transverse direction is parallel to the transverse axis. 'Width' of the article or of a component thereof, when used herein, refers to the size/distance of the dimension orthogonal to the longitudinal direction of the article or component thereof, i.e. orthogonal to the length of the article or component thereof, and typically it refers to the distance/size of the dimension parallel of the transverse axis of the article or component.

The 'Z-direction' is orthogonal to both the longitudinal and transverse directions. 'Thickness' or 'caliper' of the article or component thereof, when used herein, refers to the size/distance of the z-direction dimension. The caliper is determined under application of a 0.09 (620 Pa) pressure, as described herein.

As used herein, the term "void space" is a cavity sized to accept and contain bodily exudates such as fecal material, present in at least the relaxed sate of the article.

As used herein, 'elasticated' and 'elasticated topsheet' means, that the item or the topsheet comprises at least a portion made of elastic material, which is elastic in at least the longitudinal direction, for example including the situation that the topsheet as a whole is of elastic materials (elastically extendible in longitudinal direction) and/or that the topsheet contains elastic bands or strands, elastically extendible in longitudinal direction.

The invention is equally applicable to absorbent articles such as pull-on or training pants, pant-type diapers, incontinence briefs, incontinence undergarments, absorbent inserts, diaper holders and liners, feminine hygiene garments, bandages and the like, however, a preferred embodiment of an absorbent article of the present invention is a pull-on or training pants or diaper, preferably a diaper shown and described hereinafter. Thus, whilst the invention is described in detail with reference to a (baby, infant, or adult) diaper, this description is equally applicable to other wearable disposable article.

The disposable, wearable absorbent article, e.g. diaper, of the invention has a backsheet, which is typically liquid impervious, but preferably breathable and thereto air permeable or even moisture-vapor permeable. Any material known to be suitable as backsheet can be used herein. The backsheet, or any portion thereof, may be elastically extensible in one or more directions. In one embodiment, the backsheet may comprise a structural elastic-like film ("SELF") web. A structural elastic-like film web is an extensible material that exhibits an elastic-like behavior in the direction of elongation without the use of added elastic materials. The SELF web includes a strainable network having at least two contiguous, distinct, and dissimilar regions. SELF webs suitable for the present invention are more completely described in U.S. Pat. No. 5,518,801.

Typically, also an absorbent core is present, which is preferably positioned between at least a portion of the first topsheet and the backsheet.

The absorbent core that is preferably present, may comprise any absorbent material which is generally compressible, conformable, non-irritating to the wearer's skin, and capable of absorbing and retaining liquids such as urine and other certain body exudates, such as comminuted wood pulp, creped cellulose wadding; melt blown polymers, including coform; chemically stiffened, modified or cross-linked cellulosic fibers; tissue, including tissue wraps and tissue laminates; absorbent foams; absorbent sponges; more preferably included (at least) super absorbents (super absorbent polymers); absorbent gelling materials; or any other known absorbent material or combinations of materials. Exemplary absorbent structures for use as the absorbent core are described in U.S. Pat. Nos. 4,610,678; 4,673,402; 4,834,735; 4,888,231; 5,137,537; 5,147; 5,260,345; 5,387,207; and 5,625,222.

The article, e.g. diaper, of the invention may have side panels, and/or more preferably one or more leg cuffs that provide improved containment of liquids and other body exudates. Leg cuffs may also be referred to as leg bands, side flaps, barrier cuffs, or elastic cuffs, as described in; U.S. Pat. Nos. 3,860,003; 4,808,178 and 4,909; 4,695,278 and 4,795,454.

The diaper typically has a first or front waist region a second or back waist region, opposed to the first waist region, and a crotch region, located between the first waist region and the second waist region. The crotch region is typically that portion of the diaper which, when worn, is between the legs of the wearer. The waist regions of the diaper, when worn, typically gather or encircle the waist of the wearer and are generally at the highest at the highest elevation of the article, when the wearer is in the standing, upright position. The waist region, or preferably the waistband typically comprises the force line of the diaper.

Typically, the waist regions of the diaper have a portion, which is or forms the waistband. In one type of diapers, the waistband is open prior to use and needs fastening around the waist of the wearer. Thereto, the diaper preferably has a fastening system, typically joined to the waist region or band. The fastening system preferably maintains the first waist region and the second waist region in a touching or overlapping configuration so as to provide lateral tensions or force line about the circumference of the diaper to hold the diaper on the wearer. The fastening system preferably comprises tape tabs and/or hook and loop fastening tabs, although any other known fastening means are generally acceptable. Some exemplary fastening systems are disclosed in U.S. Pat. Nos. 3,848,594; 4,662,875; 4,846,815; 4,894,060; 4,946,527; 5,151,092; and 5,221,274; and 4,963,140.

In one alternative embodiment, the article is to be used as a pull-on type diaper, such as a training pant. Then, typically, the opposing sides of the garment may be seamed or welded to form a pant, such that the front waist portion or waistband and a back waist portion or waist band are (irremovably) connected prior to use, by a first connection area and a second connection area.

The waist regions may comprise an elastic waist feature. Such an elastic waist feature may be constructed in a number of different configurations including those described in U.S. Pat. Nos. 4,515,595; 5,151,092.

The backsheet may be attached or joined to the first topsheet, the absorbent core, or any other element of the diaper by any attachment means known in the art. The attachment means may for example include a uniform continuous layer of adhesive, a patterned layer of adhesive, or an array of separate lines, spirals, or spots of adhesive, such as disclosed in U.S. Pat. No. 4,573,986. Adhesives that have been found to be satisfactory are manufactured by H. B. Fuller Company of St. Paul, Minn. and marketed as HL-1620 and HL-1358-XZP. Alternatively, the attachment means may comprise heat bonds, pressure bonds, ultrasonic bonds, dynamic mechanical bonds, or any other suitable attachment means or combinations of these attachment means as are known in the art.

Preferred may be that the article, e.g. the diaper, includes a topical agent for the skin of the wearer, preferably on the elasticated leg cuffs, when present and/or around the opening of the second topsheet, as described hereinafter, in particular when these edges of the opening are elasticated, as described herein. Preferred agents include powders, talc, lotions, wax, as generally known in the art. It has been found to be very useful to apply such an agent, in particular talc or wax, to the elastics around the opening in the topsheet, to reduce pressure marks of the elastics on the skin of the wearer.

The article may also comprise a topical adhesive or body adhering composition that acts to hold the diaper or the first or second topsheet or the opening further in place during use. In one preferred embodiment, the topical adhesive is present on the elasticated regions along the edges of the opening. Suitable body adhesives are known in the art.

The First Topsheet

The first topsheet of the articles of the invention is made of at least a fibrous web (sheet) which has regions were the fibers are bonded and regions where the fibers are unbonded, so-called bonded and unbonded regions, respectively. The length of the first topsheet can be about equal to the length of the backsheet.

The fibers extend from one bonded region through an unbonded region to another bonded region, typically so that the fibers form loops from one bonded region to the next.

The bonded regions are such that they form the support structure for the unbonded regions, so that no backing support layer is necessary. The topsheet can thus be a single, unitary sheet or web.

Preferably, the fibers running from the same bonded region to the next same bonded region are about parallel to another.

Preferably, the bonded regions are in one plane, e.g. to form a planar support structure, and the fibers extend upward and downward out of the plane formed by the bonded region support structure, preferably in the form of loops.

The bonded regions can be in any form, provided said support structure for the unbonded regions is created. For example, a bonded region can be in the form of a dot, square, rectangle, circle, triangle, or line. A number of bonded regions can also be such that they together form a line of not connected dots, squares, lines or strips etc. In the latter case, the bonded regions should be close enough together to ensure that sufficient bonding is achieved to provide the support structure for the unbonded regions.

The unbonded regions may also for example be circular or round, square, rectangular, triangular, diamond-shaped, or hexagonal and/or oval.

The surface area of the unbonded regions when used herein is the largest convex surface area within the unbonded region, and this is at least 2 mm$^2$, preferably at least 5 mm$^2$ or even at least 10 mm$^2$, or even at least 20 mm$^2$ or even at least 25 mm$^2$, or even at least 30 mm$^2$, and typically up to 200 mm$^2$, or even up to only 100 mm$^2$.

The bonded regions have a certain width dimension, which is, when used herein, the smallest distance between two opposing sides of a bonded regions, in the plane of the topsheet or the plane which the bonded regions support structure forms (i.e. thus not the thickness dimension of the bonded regions. Typically, this width dimension is less than 3 mm, or even less than 2 mm, or even less than 1 mm, or even less than 0.8 mm, or even less than 0.5 mm.

The total surface area ratio of the total surface area of the unbonded regions and of the bonded regions is preferably: up to 20:1, or even up to 15:1, or even up to 10:1; or even up to 8:1, but preferably more than 2:1, or even more than 3:1 or even more than 4:1.

Figure 4A:
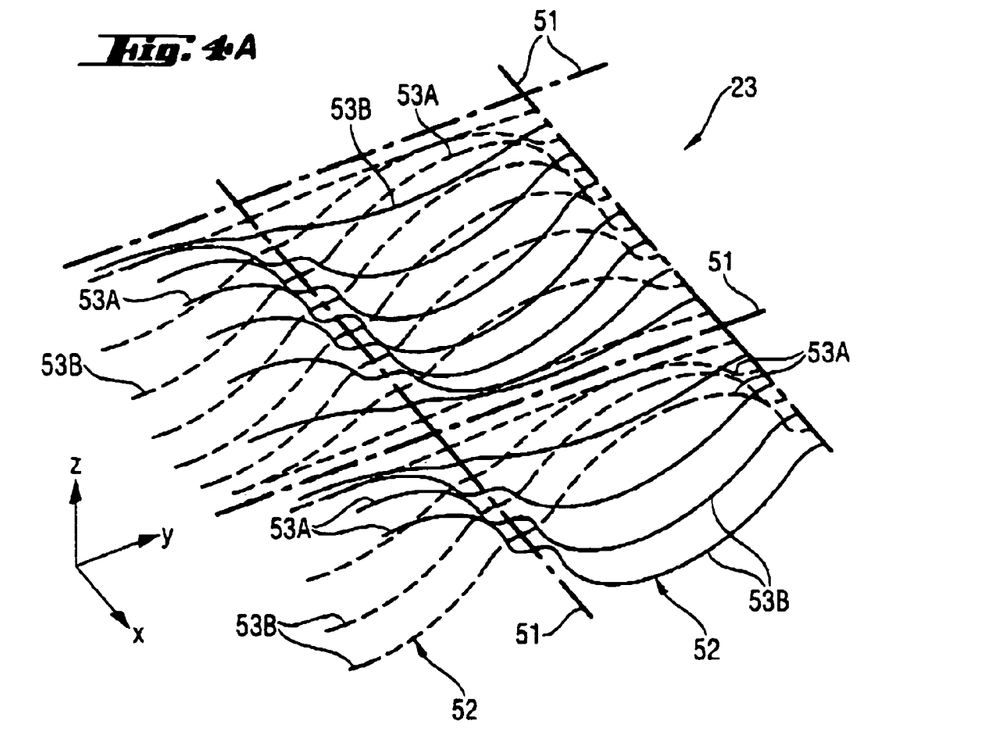
FIGS. 4a and 4b show a cross sectional view of the first topsheet of a preferred diaper of the invention.

Preferably, the bonded regions are in the form of lines, whereby preferably each bonded region (line) crosses at least one another bonded region (line). Preferably, the bonded regions are positioned in both longitudinal and transverse direction, preferably parallel to one another in each respective direction, as can be seen in FIG. 4a.

The first topsheet has a caliper or thickness of from 0.1 and 5 mm, preferably from 0.2 mm to 3 mm or even from 0.25 mm to 2 mm or even to 1 mm, as measured with 0.09 psi (620 Pa) pressure, as described hereinafter. When used herein, the caliper is the maximum caliper of the topsheet, for example measured as the average of three maximum values of three different samples, obtained via the method described herein.

In other words, the caliper of the topsheet varies, depending on whether one measures this in a bonded region or unbonded region, but the caliper when used herein is the maximum caliper of the topsheet, which will always be in an unbonded region.

The first topsheet may have any basis weight, but preferably, this is from about 10 to 45 g/m$^2$, or even from 20 to 40 g/m$^2$, or even from 30 to 35 g/m$^2$.

It may be preferred that the topsheet has a bulk density of for example 0.05 to 0.6 g/cm$^3$, or even from 0.1 to 0.4 g/cm$^3$ or even up to only 0.3 g/cm$^3$ or even up to only 0.2 g/cm$^3$.

It may be preferred that the topsheet has a porosity between 0.6 and 0.95, preferably between 0.7 and 0.9 or even between 0.8 and 0.9; and/or preferably a void volume of between 5 and 10 cm$^3$/g, or even from 6 to 9 cm$^3$/g or even from 7 to 8 cm$^3$/g.

A highly preferred first topsheet comprises or consists of a web with a caliper of about 0.25-0.29, preferably about 0.27 mm, compression resistance of about 40-60%, preferably about 55%, a basis weight of about 28-34 g/m$^2$, preferably about 32 g/m$^2$, with preferably unbonded regions of about 22 mm$^2$ to 30 mm$^2$, preferably about 25 mm$^2$, and bonded regions with a maximum width of 0.7 mm to 1.1 mm, preferably 0.9 mm, in the shape of crossing lines. Highly preferred topsheets are available from Sandler with the trade name: VP 3001/11-32gsm.

The first topsheet of the article of the invention typically has a resistance to compression (under 1 psi i.e. about 6.9×10$^3$ Pa pressure) of less than 80%, more preferred less than 70% and even more preferred less than 60%, or even less than 55%/, but it may be preferred that the resistance to compression is more than 10%, as determined by the method described herein This is in contrast with the materials described in the prior art cited above, which have a resistance to compression of well over 85%, and which are designed to retain their volume for storing BM even under pressure, and which are typically much rougher to the wearer's skin. Therefore, the first topsheet also preferably has a trans topsheet capacity of less than 3×10$^{-2}$ g/cm$^2$ (0.2 g/inch$^2$), in at least 25% of the convex topsheet area and more preferred in 100% of the topsheet area, as can be determined by the method described in U.S. Pat. No. 5,941,864.

This further ensures that the first topsheet is very soft and comfortable for the wearer. Surprisingly, the first topsheet material of the article of the invention provides excellent BM-trapping, even though it has typically a low compression resistance and typically a low trans topsheet capacity.

Preferably, the first topsheet has no large apertures in (part of) its surface. This may also help to ensure that the underlying material, typically the absorbent core and the superabsorbent or absorbent gelling material therein, cannot come in direct contact with the wearer's skin though such apertures. Thus, the first topsheet has preferably no apertures of more than 1 mm$^2$, or even no apertures of more than 0.5 mm$^2$, in 25% of its convex surface area, or preferably no such apertures anywhere in its convex surface area. Hence, unlike apertured topsheets known in the art, such as described in U.S. Pat. No. 5,342,338, the first topsheet of the article of the invention has a transtopsheet penetration of BM of less than 6×10$^{-2}$ g/cm$^2$ (or less than 0.4 g/inch$^2$ (i.e. in at least 25% of the top sheet area and more preferred in 100% of the top sheet area), as measured by the method described in U.S. Pat. No. 5,342,338.

The top sheet is preferably airpermeable, as described herein.

The first topsheet is such that it effectively traps or grabs BM, in particular runny, mucousy BM.

On one hand, a preferred first top sheet can be characterized by a very low BM transfer value, which represents the very low amount (percentage) of BM that transfers from the first topsheet back onto the skin of the wearer. On the other hand, said preferred first topsheet can be characterized by a high BM grabbing value, which represents the amount (percentage) of BM that remains in or on the diaper, when the user moves in use, e.g. when friction is applied to it.

Thus, the first top sheet has preferably a BM transfer value of less than 15%, preferably less than 12% or even less than 10%.

Moreover, the first topsheet has preferably a BM grabbing value of at least 70%, more preferably at least 75% or even at least 80% or even at least 85%.

The methods for obtaining the BM transfer and BM grabbing values are described hereinafter.

The first topsheet is preferably a carded web. Any process in the art for making carded webs can be reapplied to make the first topsheet of the article of the invention.

The fibers used the make the preferred first topsheet web typically have a length of from 30 to 100 mm or even to 70 mm, more preferably from 35 mm to 55 mm. Preferred fibers are made of polyester, viscose, or more preferably, polypropylene and/or polyethylene, or copolymers thereof. The fibers are preferably hydrophilic. The fiber dtex is preferably from 1.2 to 15, or more preferably from 1.5 to 6.

The calander design is defined by the overall pattern of the bonded and unbonded regions, including the ratio of the bonded region surface area vs unbonded region surface area, the size and number of the bonded and unbonded regions. The preferred pattern or calander design maximises the distance between bonded regions by forming geometrical figures. Calander designs can be made out of geometrical figures like circles, triangles, squares, quadrangles, diamonds, as mentioned above.

In order to optimise the caliper of the unbonded regions, it may beneficial to allow a certain thickness of the bonded regions as well; preferably the bonded regions having thus a caliper, which is from 10% to 60% or even from 20% to 40% of the caliper of the unbonded regions.

The bonding of the fibres to form the bonded regions may be done by any method. Preferably, this is done by thermobonding the fibres; alternatively, this may be done by ultrasonic bonding, which may be beneficial to obtain unbonded regions with a higher caliper than when thermo bonding techniques are used.

Second Topsheet

The article of the invention preferably also comprises a second topsheet. This is preferably a topsheet, which is placed over the wearer-facing side of the first topsheet, so that the second topsheet is the closest to the wearer's skin in use. The second topsheet is such that BM can pass through it to the first topsheet.

Preferred may be apertured topsheet such as mentioned above and describe in U.S. Pat. No. 5,342,338, having at least 25% of its convex surface with apertures of more than 1 mm$^2$ or even more than 2 mm$^2$ or even more than 4 cm$^2$, more preferably having its total surface with such apertures.

Even more preferred is that the second topsheet is a topsheet with none or more large openings to pass BM through to a void space underneath the second topsheet, e.g. between the second and first topsheet. Preferably one such opening is present. Such preferred topsheets are described in for example EP-A-1201212 and co-pending application EP01117669.0.

Preferred second topsheets are air-permeable. This is important to ensure comfortable wear to the user and to it may help reduce the risk of skin problems. The topsheet typically has an air permeability of at least 10 Darcy/mm, but more preferably at least 20 Darcy/mm or even at least 30 Darcy/mm or even at least 35 Darcy/mm. This can for example be determined by the method set out below.

The second topsheet preferably has a very low surface energy, reflected by a specific alcohol repellency value, and a uniform porosity in order to provide effective masking of the BM received through it and present on the first topsheet, and to provide in addition reduced 'back-leakage', i.e. leakage from BM received in the void space back onto the second topsheet or onto the skin of the wearer.

Therefore, the second topsheet has preferably an alcohol repellency of at least 7.0, preferred at least 8.0 more preferred at least 9.0 and most preferred the topsheet has an alcohol repellency of 10.

The second topsheet is preferably at least partially treated with a chemical, which lowers the surface energy of the second topsheet, to thus helps to provide the required masking, herein referred to as masking facilitating agent.

To obtain the second topsheets with low surface energy, i.e. high alcohol repellency, one can use any method of applying the masking facilitating agents. The method of applying the masking facilitating agent should preferably be such that a very thin coating of agent is deposited on the topsheet or part thereof, and it should be such that the air permeability and porosity is substantially unchanged. Preferred is to topically apply the masking facilitating agent to a fibrous web or to add the masking facilitating agent in molten state to the compound(s) used to make the second topsheet, e.g. to the fibers, prior to formation of the topsheet web. Thus for example, if the second topsheet is a nonwoven material made of a fiber blend, this fiber blend can comprise a masking facilitating agent in molten state, that will provide the resulting nonwoven with a high alcohol repellency and a low surface energy. The use of one or more melt-in masking facilitating agents may be combined with topical treatment with one or more masking facilitating agent, as mentioned above.

Useful agent include fluorocarbons as described in U.S. Pat. No. 5,876,753, issued to Timmons et al. on Mar. 2, 1999; U.S. Pat. No. 5,888,591 issued to Gleason et al. on Mar. 30, 1999; U.S. Pat. No. 6,045,877 issued to Gleason et al. on Apr. 4, 2000. Other agents include silicone. Useful methods for applying the agent to the second topsheet, without reducing the airpermeability, can be found in U.S. Pat. No. 5,322,729 and PCT Publication WO 96/03501.

Preferred agents may be selected from the group comprising fluorocarbons, siloxanes, polysiloxanes, preferably including fluorinated monomers and fluorinated polymers, including hexafluoroethylene, hexafluoropropylene and vinyl fluoride and vinylidene fluoride, fluoroacrylate and fluoromethacrylate. Highly preferred is that the topsheet is provided with poly(tetra)fluoroethylene, fluorinated ethylene-propylene copolymers and/or fluorinated ethylene-tetrafluoroethylene copolymers masking facilitating agent.

The masking facilitating agent is most effectively applied to fibrous nonwoven web, which comprising thermoplastic polymer fibers, preferably selected from the group comprising: polyolefins, polyesters, polyurethanes, and polyamides, most preferably the thermoplastic polymer being a polyolefin, most preferably being polypropylene or polyethylene.

In addition to the high alcohol repellency, the second topsheet preferably also has a uniform pore size distribution with small pores, i.e. the topsheet has pores with a maximum pore size of less than 100 μm preferably less than 75 μm more preferable less than 50 μm and most preferably less than 25 μm. This can be determined by the method set out hereinafter.

The pores of the second topsheet are preferably also such that the mean pore size is less than 20 μm, preferred less than 17 μm more preferred less than 13 μm and most preferred less than 10 μm.

The second topsheets of the articles of the invention, with high alcohol repellency as well as small uniformly distributed pores, also help to reduce the contamination of the skin with runny BM. This can be characterized with the BM rewet method, as set out herein.

The topsheet herein comprises preferably at least two layers one of which is a meltblown (M) layer and another is either a spunbond (S) or a carded (C) layer.

Preferred executions are SM SMS, SMMS, SSMS, SSMSS, SSMMS, CM or CMC nonwovens laminates, preferably one web being treated with a masking facilitating agent. Preferred is a laminate whereby the inner web (facing the backsheet of the article) and/or a middle web is such that the (inner surface of the) topsheet will have a low surface energy, as defined herein. For example, it is highly preferred that the topsheet comprises SMS laminate, whereby at least the meltblown web is treated such as to provide the low surface energy of the inner surface (and preferably also the outer surface) of the topsheet.

Preferably the carded and nonwoven webs are formed from polyethylene, polypropylene and/or polybutylene polymer fibers, or (a mixture of) fibers of a copolymers of polyethylene, polypropylene and/or polybutylene; most preferred are polypropylene polymer fibers.

In one embodiment of the invention, the BM rewet of the second topsheets is also less than 4.5 g, preferably below 3.5 g more preferably below 2.5 g and most preferably below 1.5 g.

The second topsheet is preferably very thin, soft and compliant; it preferably has a very low basis weight, preferably less than 35 g/m², or even less than 25 g/m², or even less than 15 g/m². It preferably has a caliper or thickness of less than 0.2 mm, or even less than 0.15 mm, or even less than 0.1 mm.

Preferred materials used for the second topsheet herein are for example a 34 gsm SMS polypropylene nonwoven laminates treated with Dipolit, having a maximum pore size (pore size) of 32 μm, an airpermeability of 34 Darcy/mm, and an alcohol repellency of 10 and a rewet of 2.8, as for example available from Pegas under the name Pegaphob 02 445 032; a 24 gsm SSMMSS polypropylene nonwoven laminates treated with Dipolit, having a maximum pore size of 57 μm, an airpermeability of 52 Darcy/mm, and an alcohol repellency of 10 and a rewet of 2.9, for example available from Pegas under the name Pegaphob 02 445 024; a 34 gsm SSMMS polypropylene nonwoven laminates treated with Dipolit, having a maximum pore size of 48 μm, an airpermeability of 42 Darcy/mm, and an alcohol repellency of 10 and a rewet of 3.0, for example available from Pegas under the name Pegaphob 02 445 032; a 20 gsm web available from Sandler under the code VP21/00/75, having a maximum pore size of 22 μm, an airpermeability of 48 Darcy/mm, and an alcohol repellency of 9 and a rewet of 1.7; a 10 gsm web available from Sandler under the code VP21/00/76, having a maximum pore size of 36 μm, an airpermeability of 95 Darcy/mm, and an alcohol repellency of 10 and a rewet of 2.1; a 20 gsm web available from Sandler under the code VP21/00/76, having a maximum pore size of 23 μm, an airpermeability of 35 Darcy/mm, and an alcohol repellency of 10 and a rewet of 1.1, the latter being most preferred.

The second topsheet typically has one or two, but preferably one opening to receive BM through. The dimensions of such an opening of the preferred second topsheet may vary, depending for example on the size of the topsheet and/or the article. The opening may extend over the full length of the topsheet. Preferred may be, in particular for size 4 diapers, that the length of the opening, e.g. in relaxed state is preferably from 5 to 30 cm, or even from 10 to 25 cm, or even from 12 to 20 cm. The width of the opening of such articles, e.g. in relaxed state, is preferably from 2 to 10 cm, more preferably 3 to 8 cm.

In a stretched state, the length of the opening may preferably be from 20 to 35 cm, and the width may preferably be from 3 to 6 cm.

The second topsheet has preferably elasticated regions, which are preferably positioned along the two longitudinal edges of the opening (so that each edge has at least one elasticated region), extending from said opening towards the first (front) and second (back) waist region, preferably such that the end portions of the elastic regions can be attached or joined to the waist region. Thus, the elasticated regions are preferably longer than the opening, both in relaxed as in stretched state. Preferred is that the elastic region is positioned over the full length of the second topsheet. The length of the elastic region will typically depend on the size of the second topsheet and/or the article. For example, for a size 4 diaper, the length of the elastic region in relaxed position may be 10 to 40 cm, or even 15 to 35, whilst in stretched position preferably from 25 to 60 or even 30 to 45 or even 35 to 40 cm.

The elastic region may be in the form of two or more substantially parallel elasticated zones, and preferred is that the elasticated regions are shaped such that the middle portions of the regions are substantially parallel to one another, whist the end portions (at least in relaxed state) bend away from one another (in the plane of the second topsheet), so that the distance between the end portions of the elastic regions is larger that the distance between the middle portions of the elastic regions. Then, the end portions of the elasticated regions make typically each an angle with the longitudinal axis of the opening, preferably each angle being between 20° and 30°, and preferably such that the angle between the end portions is about twice as much, e.g. between 40° and 60°. This is herein referred to as an X-shape. The preferred maximum distance between the elastic regions along each longitudinal edge of the opening is at least 150% of the minimum distance between the elastic regions.

Preferred is that, when in relaxed state, the elastic regions or part thereof are under an angle with the adjacent second topsheet, such that the elastic regions are (also) bending out of plane of the second topsheet, bending upwards and away from the void space (under the second topsheet).

Preferred second topsheets and processes that can be reapplied to make the diaper of the invention are for example described in EP-A-1201212.

Test Methods Referred to Herein:

Caliper (Thickness) and Compression Resistance

This test is to measure the caliper and compression resistance of the first topsheet of the articles of the invention.

The caliper as referred herein is measured by taking 3 samples of the first topsheet, e.g. about 15 cm² (1.5×1.5 square inch) each, for example by punching this out of a larger topsheet. Then, in 3 separate experiments, the maximum caliper of each sample is measured and an average is obtained and the caliper after compression is measured and averaged.

In each experiment, a sample is fixed in one position, and then a specific force is applied on the sample, and the caliper is measured with a digital caliper gauge. The caliper measurements of a sample are always done at the same spot of that sample.

Firstly, the (maximum) caliper of the first topsheet is obtained by applying a pressure of 0.09 psi (620 Pa) on the sample and measuring the maximum caliper in a certain spot.

Then, the pressure on the sample is increased to 1.0 psi ($6.9 \times 10^3$ Pa) and after 30 seconds, the caliper is measured again in the same spot; this is the compressed caliper.

This is repeated on the two other samples of the material as well, to have a total of 3 replicates. Then the average of the three obtained values of the maximum caliper at 0.09 psi (620 Pa) is calculated and this is the caliper (C) of the topsheet, as referred herein, being between 0.1 mm and 5 mm.

Also the average compressed (maximum) caliper is calculated and this is caliper ($C_p$).

Then, the compression resistance % is calculated:

$$C_p/C \times 100$$

Thus for example, a topsheet material with a caliper of 0.5 mm (the average maximum as measured at 0.09 psi (620 Pa)) and a compressed caliper of 0.25 mm (the average maximum as measured at 1.0 psi; $6.9 \times 10^3$ Pa) has a compression resistance of 50%.

BM Transfer and Grabbing Values of the First Topsheet

The BM transfer and BM grabbing values of the first topsheet can be determined as follows.

The absorbent article, e.g. diaper, is placed flat on a flat surface; if the article is elasticated, it is placed flat in fully stretched state.

First, the 100 ml of 0.9% saline solution is added at a flow rate of about 5 ml/sec. at the center point of the article and then, the article is weighed.

Then, 5 minutes after the last drop of urine was added to the article (to allow urine distribution), 10 g BM analogue 7 A (see below for composition and preparation) is added in a about square patched of 9 cm², half way between the transverse center line and the edge which would in use be at the back of the wearer, e.g., the outer edge of the back waist band.

A piece of collagen is weighed (collagen is: Kollagenfolie Natur; Articel-No. 706; cal.570/0,90m, available from Naturin GmbH & Co, Weinheim, Germany). This is used as a skin substitute. This piece needs to be large enough the be placed around a roll which has a total mass of 2 kg and a diameter of 9.0 cm and a length of 25 cm.

The roll is placed in the center of the BM loaded area and it is rolled 3 times to each side. The rolling is done such that no additional pressure (other than gravity) is applied to the roll; this is typically achieved by push-rolling the roll over the BM.

Then the roll is taken from the article and the collagen from the roll.

1) The collagen with transferred BM is weighed again. The percentage BM that is transferred to the collagen is calculated. This is the BM transfer value of the first topsheet.

2) A horizontally placed scraper blade is placed at exactly the level of the article with the remaining BM on the flat surface. The scraper blade is moved over the surface of the article, thereby removing any BM, which is not grabbed by the first topsheet.

The article with the remaining, grabbed BM is weight and the percentage remaining, grabbed BM is calculated (the original 10 grams BM being 100%).

For example, if 1.0 gram of the BM is present on the collagen (collagen weight increase is 1 gram), the BM transfer value is $1/10 \times 100\% = 10\%$.

If the article's weight increase is 8.5 gram, the BM grabbing value is $8.5/10 \times 100\% = 85\%$. (In this example, the scraper blade will have removed 0.5 gram.)

| The BM analogue 7A comprises: | |
|---|---|
| Feclone # 4* | 4.1% (by weight) |
| Feclone # 7* | 4.1% (by weight) |
| Distilled water | 90.7% (by weight) |
| Poly(acrylamide coacrylic acid)** | 1.1% (by weight) |

*available from SiliClone Studio - Doretta L. Erb - Valley Forge, PA 19481, USA.
**available from Sigma Aldrich under the code 00111TF The BM analogue 7A is prepared as follows:

A quantity of distilled water greater than what is needed to make your analogue is heated to 100° C. in a container. The appropriate amounts of Feclone 4 and 7 above are weighed and transferred to another container and thoroughly blended. Then the poly(acrylamide coacrylic acid) polymer is mixed in. Then, the water is mixed with the other ingredients to a homogenous blend.

Air Permeability

The air permeability is determined by measuring the time in which a standard volume of air is drawn through the test specimen at a constant pressure and temperature. This test is particularly suited to materials having relatively high permeability to gases, such as preferred herein, in particular nonwoven materials.

A TexTest FX3300 instrument is used. The Test Method conforms to ASTM D737. The test is operated in a laboratory environment typically about $22 \pm 2°$ C. and about $35\% \pm 15\%$ relative humidity. The test specimen has to be conditioned for at least 2 hrs. The test pressure is 125 Pascals and the test area is 38 cm². In this test, the instrument creates a constant differential pressure across the sample, which draws air through the sample. The rate of air flow through the sample is measured in ft³/min/ft² and converted to permeance (in Darcy/mm) according to the Darcy's Law:

$$K/d \text{ (Darcy/mm)} = (V \cdot \mu)/(t \cdot A \cdot \Delta p)$$

wherein k is the permeability per unit area of the specimen; V/t is the volumetric flow rate in cm³/sec; $\mu$ is the viscosity of air ($1.86 \cdot 10^{-5}$ Pa sec); d is the test material thickness in mm; A is the cross sectional area of the specimen in cm²; $\Delta p$ is the pressure differential in Pascal or Pa; and 1 Darcy=$9.869 \cdot 10^{-9}$ cm².

For each sample, three replicates should be run, and the averaged result is reported.

The area of water contact with the sample is equal to the cross sectional area of the water column, which equals 28 cm².

Alcohol Repellency (Indication for Surface Energy)

The alcohol repellency can be determined by the INDA Standard Test Method IST 80.6 (95), as published in 1996 and available from INDA, NC27513, USA. This method is used to measure the resistance of a sample to wetting and penetration of alcohol or alcohol/water solution.

The alcohol repellency value of a fabric corresponds to the highest numbered test solution, which does not penetrate the fabric. Thus, as used herein, a topsheet with an alcohol repellency of 7 is such that a test solution of 70% alcohol (anhydrous ethanol) and 30% deionised water does not penetrate through the sample, but a solution of 80% alcohol and 20% water will penetrate through.

Highly preferred is a topsheet with an alcohol repellency of 10, whereby neither a 100% alcohol solution nor any of the alcohol/water solutions penetrates though the sample.

Maximum Pore Size, Mean Pore Size and Pore Size Distribution

The maximum pore size and mean pore size, as used herein, can be calculated by use of ASTM method F316-80. As coulter porometer, required in this ASTM method, a porometer as available from PMI can be used.

Rewet Value and Method

The rewet value of the second topsheet of a preferred absorbent article of the invention can be determined by measuring the amount of BM anologue 4A which is transferred from the topsheet to dry pick-up paper under a specific pressure and this is done as follows.

The BM analogue 4A comprises:

| | |
|---|---|
| Feclone # 2* | 3.86% |
| Feclone # 4* | 3.86% |
| Ultra Dawn** | 0.62% |
| Distilled water | 91.66% |

*available from SiliClone Studio - Doretta L. Erb - Valley Forge, PA 19481, USA.
**detergent sold in the USA by The Procter&Gamble Company.

The BM analogue 4A is prepared as follows:

A quantity of distilled water greater than what is needed to make your analogue is heated to 90° C. in a container. The appropriate amounts of Feclone 2 and 4 above are weighed and transferred to another container and thoroughly blended. Then the Ultra Dawn is mixed in. Then, the water is mixed with the other ingredients to a homogenous blend.

Then, 10 g+/−0.2 g of this BM analogue 4A is put into a petri dish. A piece of the topsheet (of which the rewet value is to be determined) is placed on top of the petri dish, such that the BM analogue and the edges of the petri dish are covered. If the topsheet material has one surface, which is more fuzzy than the other surface, the more fuzzy surface is positioned upwards, away from the BM analogue.

5 plies of dry pick-up paper (10 cm*10 cm; Ahlström Grade 632 or equivalent) are weighed and then placed on top of the topsheet material.

Then, a force of 8 lbs weight is applied on the 10 cm*10 cm surface area (i.e. 0.5 psi, 3543 g per 10 cm*10 cm surface area) for 3 min.

Then, the 5 plies of pick-up paper are weighed again and the weight difference of the pick-up paper is calculated. The increase in weight X is the weight of the adhered or absorbed BM analogue on or in the pick-up paper. Then, the rewet percentage is determined by calculating what percentage X is of the initial 10 grams BM analogue. For example, if the pick-up paper weight is increased by 0.2 gram, then X is 0.2 gram and the percentage rewet or rewet value of the topsheet is: $(0.2/10) \times 100\% = 2\%$ rewet.

Preferred Diapers of the Figures

A preferred diaper of the invention is now described with reference to FIG. 1.

Figure 1:
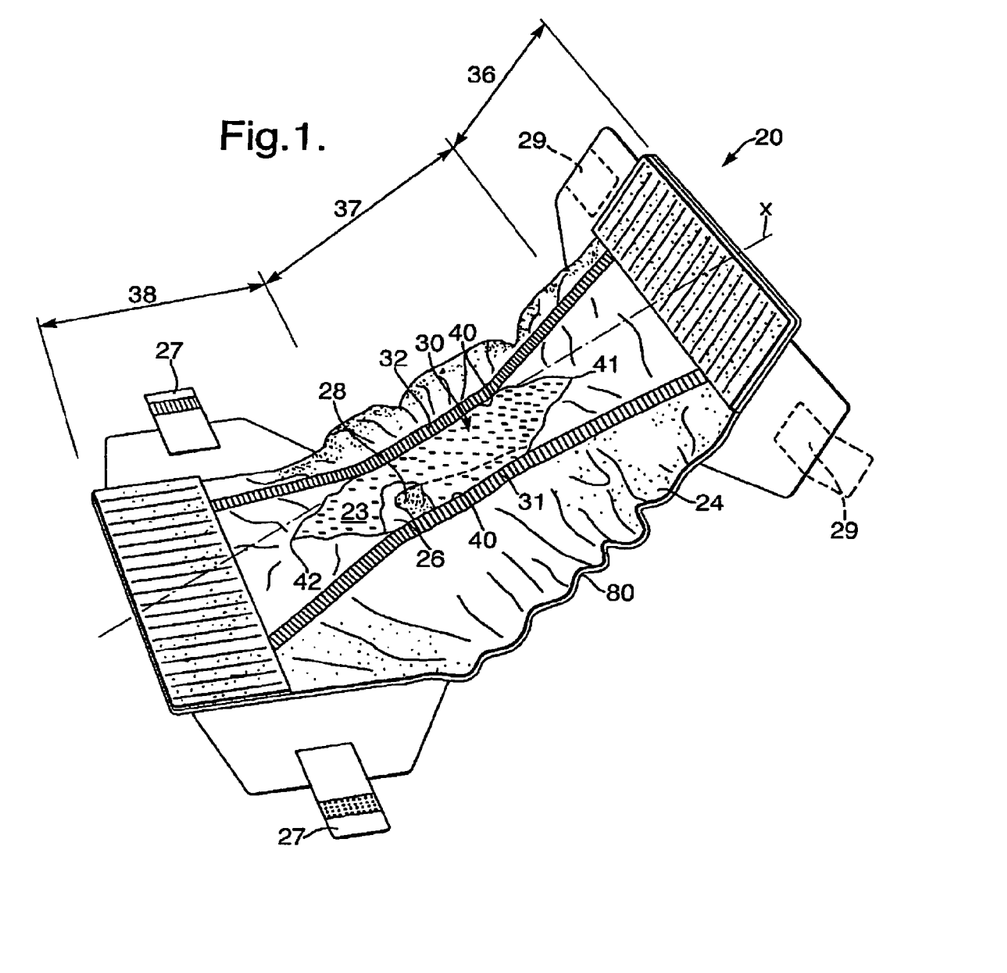
FIG. 1 is perspective view of a preferred disposable diaper of the present invention, having a first and second topsheet.

FIG. 1 is a perspective view of the diaper 20, with the portion of the diaper 20 that contacts the wearer facing the viewer. One end portion of the diaper 20 is configured as a first waist region 36 of the diaper 20. The opposite end portion is configured as a second waist region 38 of the diaper 20. An intermediate portion of the diaper 20 is configured as a crotch region 37 that extends longitudinally between the first and second waist regions 36 and 38. The waist regions 36 and 38 generally comprise those waist portions of the diaper 20 which, when worn, encircle the waist of the wearer. The waist regions 36 and 38 includes elements which can gather about the waist of the wearer to provide improved fit and containment, or which typically can gather around the waist and can be fastened around the waist by use of fastening means, such as tabs 27, which are fastened to landing zones 29. The crotch region 37 is that portion of the diaper 20 which, when the diaper 20 is worn, is generally positioned between the legs of the wearer. The diaper 20 comprises a second topsheet 24, a first topsheet 23, a liquid impervious backsheet 26, and an absorbent core 28 encased between the first topsheet 23 and the backsheet 26.

Figure 2:
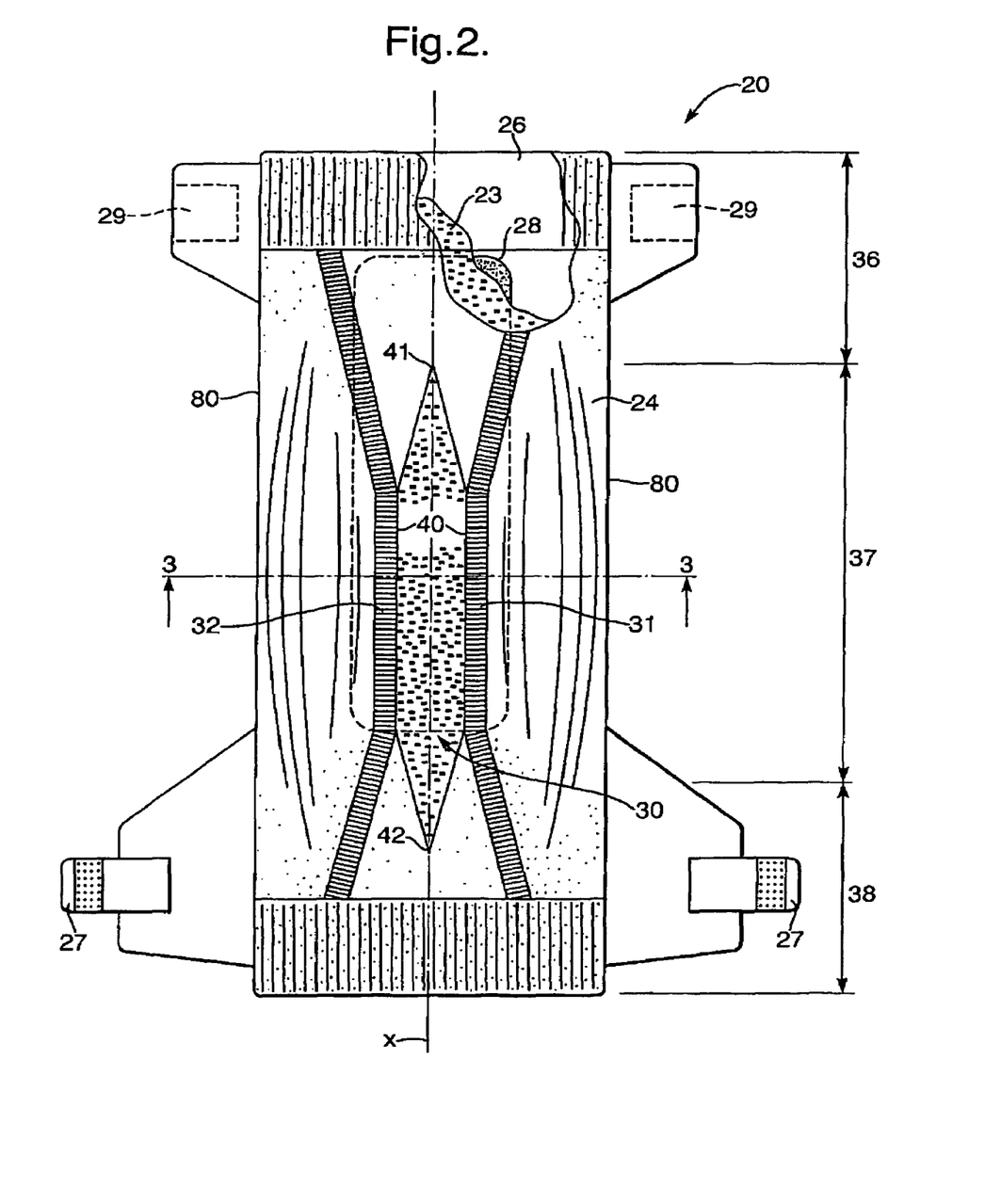
FIG. 2 is a plane view of a preferred diaper of the invention.

FIG. 2 shows a planar view of the diaper 20 of FIG. 1 in fully stretched state. In this execution, the slit opening 30 is such that the first topsheet 23 is still visible and this topsheet 23 is thus capable of being partially in direct contact with the wearer in use, although the diaper 20 may be applied such that the direct contact does not occur in use.

As can be seen in FIGS. 1 and 2, the second topsheet 24 comprises a slit opening 30, along the longitudinal axis x of the diaper 20, which is configured to receive fecal exudates and isolate at least a portion of the exudates from the skin of the wearer. In FIG. 1, the topsheet 24 is partially elasticated by the provision of elastic bands 31 and 32, which have an X-shape.

The slit opening 30 is located in the second topsheet 24 such that the fecal exudates pass through the opening into a void space formed between the second topsheet 24 and the first topsheet 23. The void space entraps or encapsulates bodily waste.

The slit opening 30 in the topsheet 24 is located in alignment with the wearer's anus during use. Preferably, the slit opening 30 in the topsheet 24 is located in a target zone of the diaper. Particularly, in one non-limiting embodiment, the target zone may extend from about 5 to about 30 centimeters in length along the longitudinal axis x of the diaper with about one fourth of its length extending longitudinally from the lateral axis y of the diaper 20 towards the first or front waist region 36 and the remainder extending longitudinally towards the second or back waist region 38, when measurements are made with the topsheet in a fully extended or stretched state. Generally, 20% to 30% of the slit opening 30 may be located forward of the lateral centerline on the diaper 20.

The slit opening 30 in the topsheet 24 is generally disposed in the target zone along the longitudinal axis x and is defined by two opposing longitudinally extending side edges 40, a front edge 41 and a back edge 42. The front edge 41 is generally located in the crotch region 37 of the diaper 20 towards the first, front region 36, or in the first waist region 36 itself, while the back edge 42 is located in the crotch region 37 near the second waist region 38, or in the second waist region 38 itself.

The diaper 20 preferably also includes a fastening system, typically including at least one engaging component (or fastener of male fastening component) 27 and at least one landing zone 29 (female fastening component), such as hook-loop type fastening systems.

The topsheet 24 including elasticated regions 31 and 32, along at least portions of the longitudinal edges 40 of the slit opening 30. The elastic regions 31 and 32 ensure that the opening 30 of the diaper 20 is positioned and remains positioned correctly. The elasticated regions 31, 32 may be formed by bonding pre-stretched elastic bands along the longitudinal edges 40 of the slit opening 30, by the method described herein.

It may be more preferred that the article has a slit opening which has a hexagonal shape, as can be seen in FIGS. 1 and 2.

The diaper 20 also preferably has leg cuffs 80 on both longitudinal edges of the diaper 20, typically attached to the backsheet 26. Preferred is that the longitudinal edge of a leg cuff 80, the longitudinal edge of the topsheet 24 and the longitudinal edge of the backsheet 26 are attached together in the form of a thin, longitudinal attachment edge.

Figure 3:
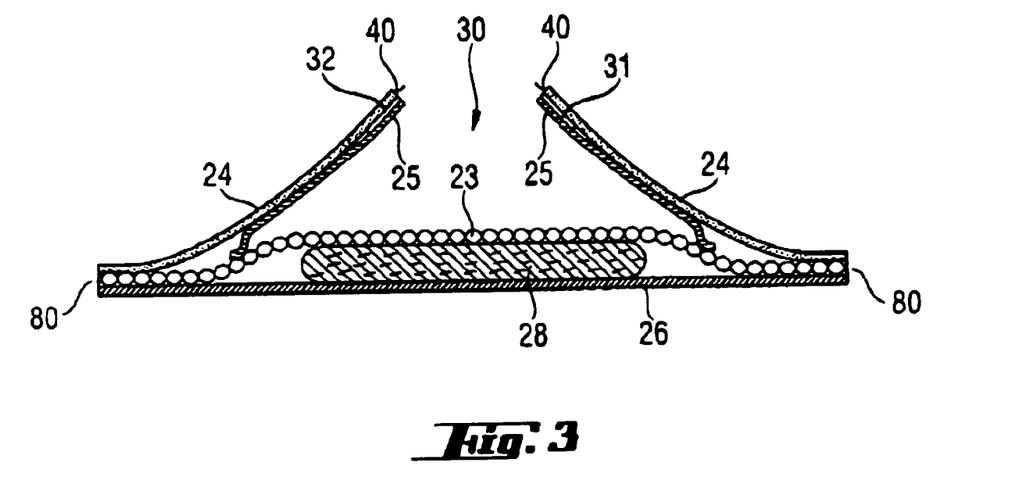
FIG. 3 is a cross section of the preferred diaper of the invention of FIG. 2.

FIG. 3 shows a cross section of the diaper of FIG. 2. The first topsheet 23 overlays the core 28 and is partially covered by the second topsheet 24. Second topsheet 24 comprises elastics 31, 32, preferably positioned such that there is no direct contact between the elastics 31, 32 and the skin of the wearer in use. The first topsheet 23 may enclose the absorbent core 28 completely, or it may be a web that only covers the top of the absorbent core 28, as can be seen in FIG. 3. The topsheet 23 may be attached to the backsheet 26 only, or to the second topsheet 24 only, or to both. The bonding to the backsheet 26 and second topsheet 24 may be in one bonding line, bonding the first topsheet 23 and second topsheet 24 and the backsheet all together, or in different bonding lines, for example one bindng the first topsheet 23 and the backsheet 26 and one binding the first topsheet 23 and the second topsheet 24 (e.g. in either case typically around the periphery of the first topsheet 23 and the backsheet 26 and/or the second topsheet 24)

FIG. 3 also shows the preferred execution whereby an additional cuff-layer 25 is present, which forms an additional barrier against BM received through the opening 30, and which reduces leakage of BM from the diaper through the sides, e.g. through the peripheral areas where the topsheets 23, 24 and the backsheet 26 are bonded to one another. The extra cuff-layer extends from about the edge 40 of the opening 30 of the second topsheet 24 towards the peripheral edge of the second topsheet 24, typically running about parallel to the second topsheet 24, and typically such that it is bonded to the first topsheet 23 inwards from the bonding of the second topsheet 24 and backsheet 26, and/or such that it is bonded to the first topsheet 23 at a separate bonding point than where first topsheet 23 is bonded to the second topsheet 24 and/or backsheet 26.

In FIG. 3, the extra cuff-layer 25 is extendible, so that this layer 25 can move along with the second tophseet 24, e.g. if the second topsheet 24 becomes more vertically, due to the pulling forces of BM in the diaper 20, the extra cuff-layer 25 can move also more vertically. The extra cuff layer 25 may for example be stretchable, e.g. elastically stretchable; alternatively or in addition, the extra cuff-layer 25 can have folds in the part, which is not attached to the second or first topsheet 24, 23, which can unfold when needed, e.g. when the extra cuff-layer needs to move to a more vertical position, along with the first topsheet 24.

In a preferred execution the extra cuff-layer 25 serves to place the elastics 31, 32 onto the first topsheet 23 and the extra cuff-layer 25 is then attached to the first topsheet 23 after the elastics 31, 32 are placed on the inside of topsheet 24.

Figure 4B:
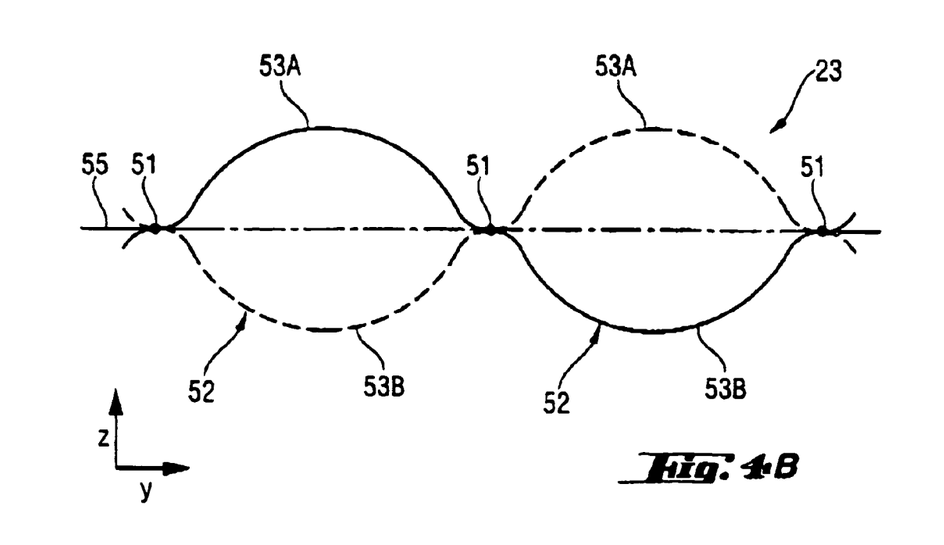

The first topsheet 23 can be better understood from FIGS. 4A and B. The first topsheet 23 is a, preferably carded, web of fibers 53A and 53B, with bonded regions 51 and unbonded regions 52. The bonded regions 51 have a planer configuration; in other words, form a plane 55 of bonded regions. The fibers 53A are in the form of loops, extending upward out of the plane 55, formed by the bonded regions 51 and fibers 53B in the form of loops downward out of said plane 55. The first topsheet may comprise fibers, which do not terminate in a bonded region, i.e. whereof the end portion is unbonded. Then, the end portion may be in the shape of a partial loop, but depending on the length of the free end portion of the fiber, it may be oriented out of the plane, for example in direction. Typically, the length of the end portion of a fiber, when this does not terminate in a bonded region, is up to 25% of the total length of the fiber, preferably up to 20%, or even up to 10%.

The bonded regions 51 are preferably in the form of strips, which preferably cross one another. Preferred may be that the bonded regions 51 are both in longitudinal (x) direction and in transverse (y) direction; preferably in the form of parallel strips in transverse direction and parallel strips in longitudinal direction.

Preferred properties and features of the first topsheet 23 are described above. Highly preferred topsheets are available from Sandler with the trade name: VP 3001/11-32gsm.

What is claimed is:

1. A disposable absorbent article with a backsheet and a first topsheet, which in use is capable of being at least partially in contact with a wearer's skin, said first topsheet being a unitary three-dimensional web of fibers with no backing, having a width, length and thickness (caliper) dimension, said unitary three-dimensional web having bonded regions, where the fibers are bonded to one another, and unbonded regions, where the fibers are unbonded to one another, wherein the fibers extend from at least one bonded region through at least one unbonded region to at least one other bonded region and wherein the bonded regions form a support structure for the unbonded regions and each of the unbonded regions has a surface area of at least 2 mm$^2$ and wherein the topsheet has a thickness (caliper) of between 0.1 and 5 mm, wherein the support structure defines a plane having a first side and a second side disposed opposite the first side;

wherein a plurality of the fibers extending through the unbonded regions define loops;

wherein each one of the plurality of fibers:

extends from a first bonded region outward from the plane away from the first side and curves to extend toward the first side of the plane;

passes through a second bonded region and extends outward from the plane away from the second side and curves to extend toward the second side of the plane; and passes through a third bonded region and extends outward from the plane away from the first side; and wherein the unitary three-dimensional web of fibers defines a convex surface area wherein at least 25% of the convex surface area has no apertures having an area of more than 1 mm$^2$; and wherein the first topsheet has a BM transfer value of less than 15%, a BM grabbing value of at least 75%, and a resistance to compression greater than 10% and less than 35%.

2. The disposable absorbent article of claim 1, wherein the surface area of the unbonded regions is more than 20 mm$^2$, and the bonded regions have a width dimension that is less than 5 mm.

3. The disposable absorbent article of claim 1 further comprising a second topsheet, positioned over the body-facing side of the first topsheet, said second topsheet having an opening, which provides a passageway to a primary void space for receiving bodily exudates therein, said void space being positioned between the second topsheet and the first topsheet, and wherein the second topsheet is elasticated.

4. The disposable absorbent article of claim 3, wherein said second topsheet comprises at least one sheet of fibrous material with a uniform pore size distribution and with a maximum pore size of less than 100 μm, and wherein said second topsheet has an air-permeability of at least 3 Darcy/mm, and wherein said second topsheet has an alcohol repellency of at least 7.0.

5. The disposable absorbent article of claim 1, the first topsheet and the backsheet having lengths that are about equal.

6. The disposable absorbent article of claim 1, wherein the first topsheet has a Trans Topsheet Capacity of less than 0.2 g/inch$^2$ in at least 25% of the convex surface area.

7. The disposable absorbent article of claim 1, wherein the first topsheet has a Trans Topsheet Penetration of less than $6 \times 10^{-2}$ g/cm$^2$ in at least 25% of the convex surface area.

8. The disposable absorbent article of claim 1, wherein the first topsheet is a carded web.

9. The disposable absorbent article of claim 1, wherein the surface area of the unbonded regions is more than 30 mm$^2$, and the bonded regions have a width dimension that is less than 5 mm.

10. The disposable absorbent article of claim 1, wherein at least 25% of the convex surface area has no apertures having an area of more than 0.5 mm$^2$.

11. The disposable absorbent article of claim 3, wherein said second topsheet comprises at least one sheet of fibrous material with a uniform pore size distribution and with a maximum pore size of less than 50 μm and wherein said second topsheet has an air-permeability of at least 3 Darcy/mm, and wherein said second topsheet has an alcohol repellency of at least 7.0.

12. The disposable absorbent article of claim 3, wherein said second topsheet comprises at least one sheet of fibrous material with a uniform pore size distribution and with a maximum pore size of less than 50 μm and wherein said second topsheet has an air-permeability of at least 20 Darcy/mm, and wherein said second topsheet has an alcohol repellency of at least 10.0.

13. The disposable absorbent article of claim 1, wherein the surface area of the unbonded regions is more than 40 mm$^2$, and the bonded regions have a width dimension that is less than 1 mm.

14. The disposable absorbent article of claim 1, wherein the bonded regions are in the form of a line of not connected dots, not connected squares, or not connected lines.

15. The disposable absorbent article of claim 1, wherein the bonded regions are in the form of lines and at least one bonded region crosses another bonded region.

* * * * *

UNITED STATES PATENT AND TRADEMARK OFFICE
CERTIFICATE OF CORRECTION

PATENT NO. : 7,597,689 B2  
APPLICATION NO. : 10/703233  
DATED : October 6, 2009  
INVENTOR(S) : Hoffmann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 709 days.

Signed and Sealed this

Twenty-eighth Day of September, 2010

David J. Kappos  
*Director of the United States Patent and Trademark Office*